US010993056B1

(12) United States Patent
Schumaier

(10) Patent No.: US 10,993,056 B1
(45) Date of Patent: Apr. 27, 2021

(54) PREPROGRAMMED HEARING ASSISTANCE DEVICE WITH PRESELECTED ALGORITHM

(71) Applicant: Daniel R. Schumaier, Elizabethton, TN (US)

(72) Inventor: Daniel R. Schumaier, Elizabethton, TN (US)

(*) Notice: Subject to any disclaimer, the term of this patent is extended or adjusted under 35 U.S.C. 154(b) by 0 days.

(21) Appl. No.: 16/598,190

(22) Filed: Oct. 10, 2019

(51) Int. Cl.
*H04R 25/00* (2006.01)
*A61B 5/12* (2006.01)

(52) U.S. Cl.
CPC .............. *H04R 25/70* (2013.01); *A61B 5/123* (2013.01); *H04R 25/505* (2013.01); *H04R 25/558* (2013.01); *H04R 2225/55* (2013.01)

(58) Field of Classification Search
CPC ........ H04R 25/00; H04R 25/55; H04R 25/558
USPC .................................. 381/312, 315
See application file for complete search history.

(56) References Cited

U.S. PATENT DOCUMENTS

| 7,974,716 | B2 | 7/2011 | Schumaier |
| 8,077,890 | B2 | 12/2011 | Schumaier |
| 8,265,314 | B2 | 9/2012 | Schumaier |
| 8,284,968 | B2 | 10/2012 | Schumaier |
| 8,396,237 | B2 | 3/2013 | Schumaier |
| 8,472,634 | B2 | 6/2013 | Schumaier et al. |
| 8,811,642 | B2 | 8/2014 | Schumaier |
| 2013/0058512 | A1 | 3/2013 | Schumaier |
| 2016/0174001 | A1* | 6/2016 | Ungstrup ............ H04R 25/554 |
| | | | 381/315 |
| 2016/0183009 | A1* | 6/2016 | Kim .................... H04R 25/30 |
| | | | 381/315 |
| 2016/0255447 | A1* | 9/2016 | Kim .................... H04R 25/70 |
| | | | 381/315 |
| 2019/0149928 | A1* | 5/2019 | Porsbo ................ H04R 25/30 |
| | | | 381/315 |

FOREIGN PATENT DOCUMENTS

| CN | 103491491 A | 1/2014 |
| WO | 2008134345 A1 | 11/2008 |
| WO | 2014070547 A1 | 5/2014 |
| WO | 2016022905 A1 | 2/2016 |

OTHER PUBLICATIONS

Extended European Search Report for EP app. No. 20199731.9, dated Mar. 4, 2021, 6 pages.

* cited by examiner

*Primary Examiner* — Suhan Ni
(74) *Attorney, Agent, or Firm* — Luedeka Neely Group, P.C.

(57) ABSTRACT

A method for programming a hearing assistance device includes entering an audiogram into the memory of a mobile computing device, wherein the audiogram indicates a hearing loss profile of a user of the hearing assistance device. Based on the audiogram, the mobile computing device determines a preferred hearing correction algorithm for the user and transfers the preferred algorithm to the memory of the hearing assistance device, which also contains one or more preloaded hearing correction algorithms. During an initial setup procedure, the user listens to sounds amplified by the hearing assistance device while switching between the preferred algorithm and the preloaded algorithms, and selects the algorithm that sounds best for continued use in the hearing assistance device.

20 Claims, 4 Drawing Sheets

| | | Frequency (Hz) | | | | | | | | |
|---|---|---|---|---|---|---|---|---|---|---|
| | | 250 | 500 | 750 | 1000 | 1500 | 2000 | 3000 | 4000 | 6000 | 8000 |
| Hearing Threshold Level (dB) | Left | 40 | 35 | | 45 | | 55 | 50 | 55 | | 65 |
| | Right | 35 | 30 | | 45 | | 55 | 45 | 50 | | 75 |

PREPROGRAMMED HEARING ASSISTANCE DEVICE WITH PRESELECTED ALGORITHM

FIELD

This invention relates to the field of hearing assistance devices, such as hearing aids and personal sound amplifiers. More particularly, this invention relates to a system for programming a hearing assistance device.

BACKGROUND

User programmable hearing aids are now in wide use. Such hearing aids come preprogrammed from the manufacturer with several hearing correction algorithms from which the user can choose to accommodate the acoustic environment that the user is experiencing at any given time. Since these programmable hearing aids come preloaded with hearing correction algorithms designed for use by persons having widely-varying hearing loss profiles in a wide range of acoustic environments, such algorithms are not finetuned for individual users. This leads to less than optimal hearing correction results for many users of such devices.

What is needed, therefore, is a user programmable hearing assistance device that is preprogrammed with selectable hearing correction algorithms that are best suited for correction of each user's individual hearing loss characteristics.

SUMMARY

The above and other needs are met by a method for programming a programmable hearing assistance device. A first embodiment of the method includes the following steps:
- (a) receiving a hearing loss profile of a user of the programmable hearing assistance device;
- (b) based at least in part on the hearing loss profile, determining a preferred hearing correction algorithm for the user;
- (c) storing the preferred hearing correction algorithm in memory of the programmable hearing assistance device, into which one or more preloaded hearing correction algorithms were previously stored;
- (d) after completion of step (c), delivering the programmable hearing assistance device to the user;
- (e) during an initial setup procedure, the user listening to sounds amplified by the programmable hearing assistance device while switching between the preferred hearing correction algorithm and the one or more preloaded hearing correction algorithms; and
- (f) the user selecting the preferred hearing correction algorithm or one of the preloaded hearing correction algorithms for continued use in the programmable hearing assistance device, wherein the algorithm selected in step (f) comprises a selected algorithm that continues to be used in the programmable hearing assistance device after completion of the initial setup procedure.

In some embodiments, step (e) includes:
- (e1) the user listening to sounds amplified by the programmable hearing assistance device while switching between the preferred hearing correction algorithm and one or more first preloaded hearing correction algorithms;
- (f1) the user selecting the preferred hearing correction algorithm or one of the first preloaded hearing correction algorithms;
- (e2) the user listening to sounds amplified by the programmable hearing assistance device while switching between the algorithm selected in step (f1) and one or more second preloaded hearing correction algorithms; and
- (f2) the user selecting the algorithm selected in step (f1) or one of the second preloaded hearing correction algorithms for continued use in the programmable hearing assistance device.

In some embodiments, the hearing loss profile received in step (a) is generated by an audiologist.

In some embodiments, the hearing loss profile comprises an audiogram.

In some embodiments, steps (a) through (c) are performed by a hearing assistance device programming entity, such as a manufacturer of the programmable hearing assistance device or an audiologist.

In some embodiments, the selected algorithm continues to be used each time power is applied to the programmable hearing assistance device until the programmable hearing assistance device is reset or reprogrammed.

In some embodiments, the switching and selecting of steps (e) and (f) are performed by the user while interacting with an interface of a mobile computing device, such as a smart phone or tablet computer executing a setup and control application.

A second embodiment of the method includes the following steps:
- (a) entering an audiogram into memory of a mobile computing device, the audiogram indicating a hearing loss profile of a user of the programmable hearing assistance device;
- (b) based at least in part on the audiogram, a processor of the mobile computing device determining a preferred hearing correction algorithm for the user;
- (c) communicating the preferred hearing correction algorithm from the mobile computing device to memory of the programmable hearing assistance device;
- (d) storing the preferred hearing correction algorithm in memory of the programmable hearing assistance device, wherein the memory of the programmable hearing assistance device also contains one or more preloaded hearing correction algorithms;
- (e) during an initial setup procedure, the user listening to sounds amplified by the programmable hearing assistance device while switching between the preferred hearing correction algorithm and the one or more preloaded hearing correction algorithms; and
- (f) the user selecting the preferred hearing correction algorithm or one of the preloaded hearing correction algorithms for continued use in the programmable hearing assistance device.

In some embodiments, the algorithm selected in step (f) continues to be used each time power is applied to the programmable hearing assistance device until the programmable hearing assistance device is reset or reprogrammed.

In some embodiments, the switching and selecting of steps (e) and (f) are performed by the user while interacting with an interface of the mobile computing device.

In some embodiments, the interface of the mobile computing device comprises a graphical user interface displayed on a display screen of the mobile computing device.

In some embodiments, the mobile computing device is in wireless communication with the programmable hearing assistance device, and step (c) is performed wirelessly.

In some embodiments, the mobile computing device comprises a smart phone or tablet computer executing a setup and control application.

In some embodiments, the one or more preloaded hearing correction algorithms were loaded into the memory of the programmable hearing assistance device prior to step (d).

In another aspect, embodiments of the invention provide a memory storage device on which computer-executable instructions are stored for downloading to and execution by a processor of a mobile computing device to program a programmable hearing assistance device. In one embodiment, the computer-executable instructions include instructions for:

- entering an audiogram into memory of the mobile computing device, the audiogram indicating a hearing loss profile of a user of the programmable hearing assistance device;
- determining a preferred hearing correction algorithm for the user based at least in part on the audiogram;
- communicating the preferred hearing correction algorithm from the mobile computing device to the programmable hearing assistance device;
- controlling the programmable hearing assistance device to store the preferred hearing correction algorithm in memory of the programmable hearing assistance device;
- based on input from the user, controlling the programmable hearing assistance device to switch between the preferred hearing correction algorithm and multiple preloaded hearing correction algorithms stored in the memory of the programmable hearing assistance device while the user listens to sounds amplified by the programmable hearing assistance device while; and
- based on input from the user, selecting the preferred hearing correction algorithm or one of the preloaded hearing correction algorithms for continued use in the programmable hearing assistance device.

In some embodiments, the computer-executable instructions include instructions for generating a graphical user interface displayed on a display screen of the mobile computing device, wherein the graphical user interface receives the input from the user.

In some embodiments, the computer-executable instructions include instructions for wirelessly communicating the preferred hearing correction algorithm from the mobile computing device to the programmable hearing assistance device.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
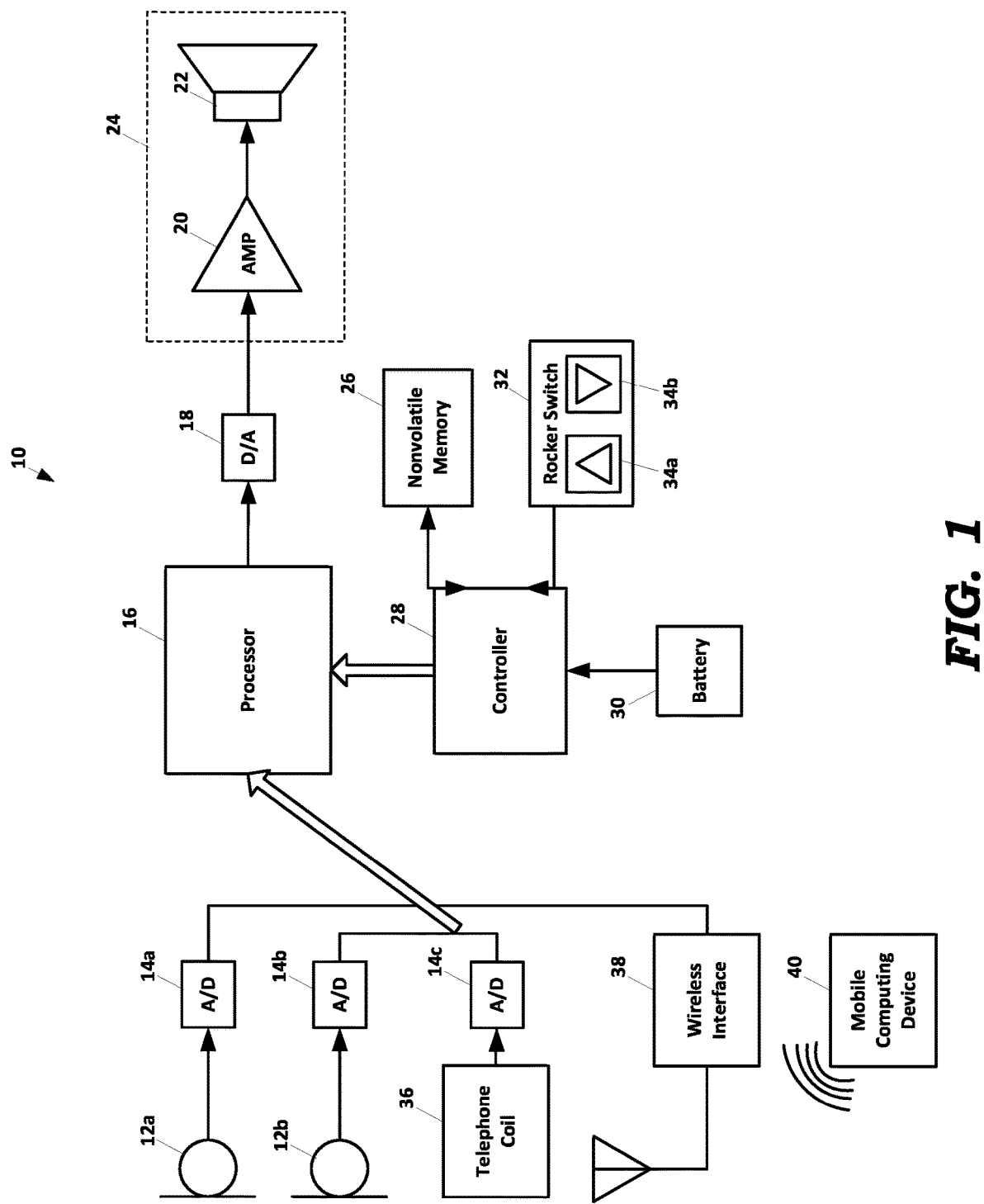
FIG. 1 depicts a functional block diagram of a personal hearing assistance device according to a preferred embodiment.

FIG. 1 depicts a preferred embodiment of a personal hearing assistance device 10 for amplifying ambient sound. The device 10 preferably includes two microphones 12a-12b for sensing sound and converting the sound to analog audio signals. The analog audio signals generated by the microphones 12a-b are converted to digital audio signals by analog-to-digital (A/D) converters 14a-14b. The digital audio signals are processed by a digital processor 16 to shape the frequency envelope of the digital audio signals to enhance those signals to improve their audibility for a user of the device 10. Further discussion of various programs for processing the digital audio signals by the processor 16 is provided below. Thus, the processor 16 generates digital audio signals that are modified based on the programming of the processor 16. The modified digital audio signals are provided to a digital-to-analog (D/A) converter 18 which generates analog audio signals based on the modified digital audio signals. The analog audio signals at the output of the D/A converter 18 are amplified by an audio amplifier 20, where the level of amplification is controlled by a control device 32, such as a rocker switch, coupled to a controller 28. The amplified audio signals at the output of the amplifier 20 are provided to a sound generation device 22, which may be an audio speaker or other type of transducer that generates sound waves or mechanical vibrations that the user perceives as sound. The amplifier 20 and sound generation device 22 are referred to collectively herein as an audio output section 24 of the device 10. The device is preferably powered by a replaceable or rechargeable battery 30.

In a preferred embodiment, the control device 32 comprises a digital rocker switch mounted on an outer surface of a housing of the device 10. For example, the digital rocker switch 32 may be a model number MT90 Momentary Toggle Switch manufactured by Sonion. In some embodiments, the control device 32 comprises two individual push button switches disposed in a single rocker-style switch housing. Both of these control device configurations are referred to herein as a digital rocker switch and both include "up" and "down" controls 34a and 34b. The digital rocker switch 32 is also referred to herein as a multipurpose control device because it may be used as a volume control and as a control for switching between and selecting audio processing programs. As described in more detail below, the rocker switch 32 may be used in conjunction with closure of a battery compartment door to reset the device 10.

In a preferred embodiment, the rocker switch 32 is used to select preferred quiet environment programs during a setup procedure, to switch between a quiet environment program, noisy environment program, and telecoil program during daily use, to control audio volume during daily use, and to reset the device 10.

The device 10 may be configured as a behind-the-ear (BTE) instrument, with the rocker switch 32 located on an accessible surface of the housing of the BTE instrument. However, it will be appreciated that the invention is not limited to any particular configuration of the device 10. In various embodiments, the device 10 may comprise an open fit device, an ear canal device, a half-shell configuration, a BTE device, an in-the-ear (ITE) device or a completely in canal (CIC) device.

Nonvolatile memory 26, such as read-only memory (ROM), programmable ROM (PROM), electrically erasable PROM (EEPROM), or flash memory, is provided for storing programming instructions and other operational parameters for the device 10. Preferably, the memory 26 is accessible by the processor 16 and/or the controller 28.

According to preferred embodiments, the personal sound amplification device 10 is operable in several different modes as determined by its programming. As the terms are used herein, "programs" and "programming" refers to one or more sets of instructions or parameters that are carried out or used by the processor 16 in shaping the frequency envelope of digital audio signals to enhance those signals to improve audibility for the user of the device 10. "Programs" and "programming" also refers to the instructions carried out by the processor 16 in determining which of several stored enhancement programs provides the best improvement for the user.

As used herein, a program is a set of instructions that implement an amplification algorithm for setting the audio frequency shaping or compensation provided in the processor 16. The amplification algorithms may also be referred to as "gain-frequency response" algorithms. Examples of generally accepted gain-frequency response algorithms include NAL (National Acoustic Laboratories; Bryne & Tonisson, 1976), Berger (Berger, Hagberg & Rane, 1977), POGO (Prescription of Gain and Output; McCandless & Lyregaard, 1983), NAL-R (NAL-Revised; Byrne & Dillon, 1986), POGO II (Schwartz, Lyregaard & Lundh, 1988), NAL-RP (NAL-Revised, Profound; Byrne, Parkinson & Newall, 1991), FIG6 (Killion & Fikret-Pasa, 1993) and NAL-NL1 (NAL nonlinear; Dillon, 1999). It will be appreciated that other algorithms could be used in association with the methods described herein, and the above list should not be construed as limiting the scope of the invention in any way.

In the preferred embodiment of the invention, a feedback canceller algorithm is also stored in the memory 26 of the device 10. An example of a feedback canceller algorithm is described in U.S. Patent Application Publication 2005/0047620 by Robert Fretz. As described in more detail below, such an algorithm is used to set the acoustical gain levels in the processor 16 and/or the amplifier 20 to avoid audio feedback in the device 10.

With continued reference to FIG. 1, some embodiments include a telephone coil 36. The telephone coil 36 is small coil of wire for picking up the magnetic field emitted by the ear piece of some telephone receivers or loop induction systems when the hearing assistance device 10 is disposed near such a telephone receiver or loop induction system. Signals generated by the telephone coil 36 are converted to digital signals by an A/D converter 14c and are provided to the processor 16. As discussed in more detail below, the converted digital signals from the telephone coil 36 may be used in some embodiments for resetting or reprogramming the processor 16, or controlling the operation of the hearing assistance device 16 in other ways.

Some embodiments of the invention also include a wireless interface 38, such as a Bluetooth interface, for receiving wireless signals for resetting or reprogramming the processor 16. In some embodiments, a mobile computing device 40 communicates with the wireless interface 38 to control the setup and operation of the device 10, including the selection of acoustical configuration programs or masking stimuli programs. For example, the mobile computing device 40 may be a smartphone, tablet, or laptop computer, running a setup and control application. The wireless interface 38 may also be used to wirelessly deliver an audio signal to the device 10, such as a music signal transmitted from a wireless transmitter attached to a CD player, or the audio portion of a television program transmitted from a wireless transmitter connected to a television tuner. In various embodiments, the wireless interface 38 comprises a WiFi link according to the IEEE 802.11 specification, a Bluetooth link, an infrared link, or other wireless communication link.

Figure 2:
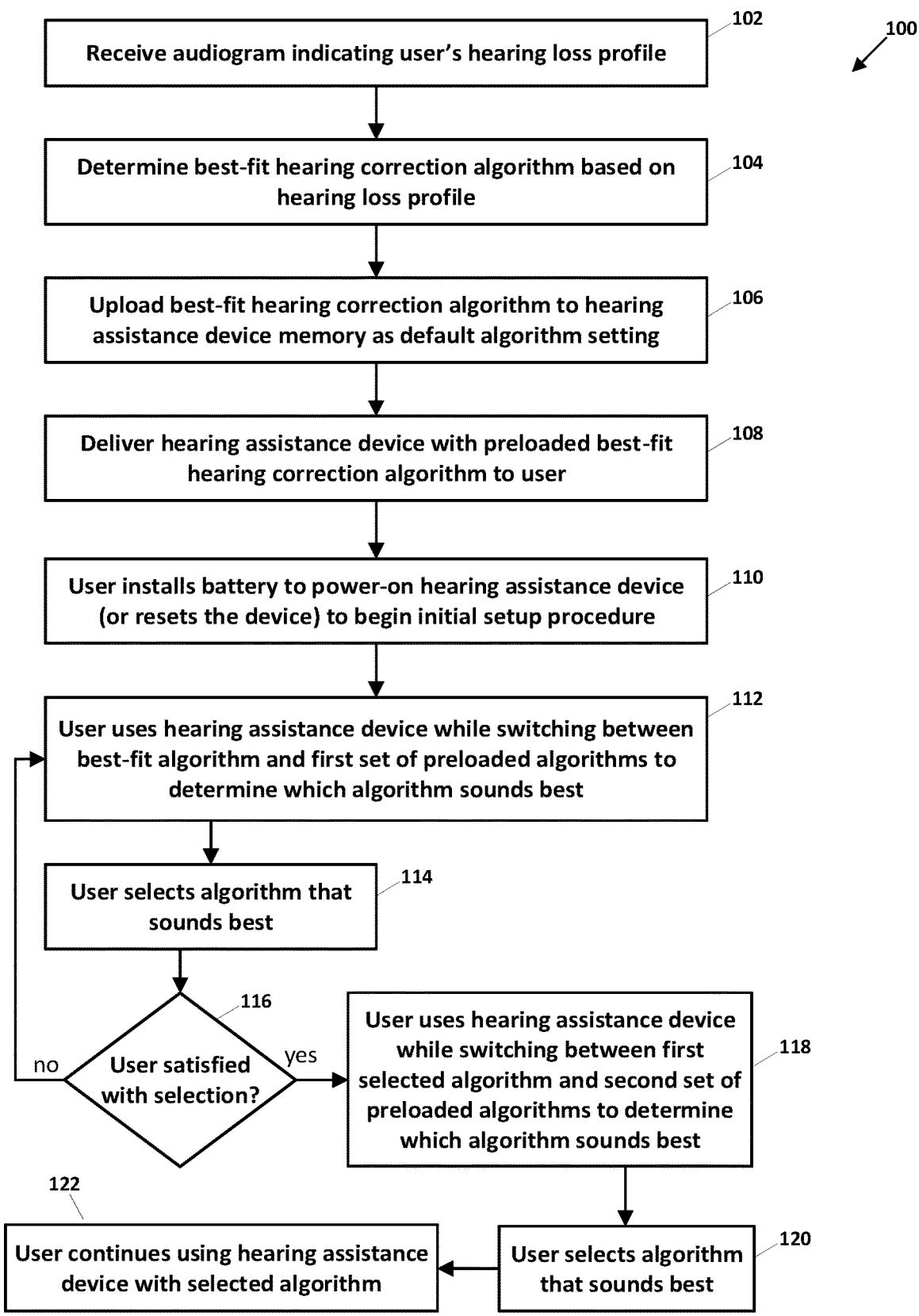
FIG. 2 depicts a functional flow diagram of the operation of a personal hearing assistance device according to a preferred embodiment.

FIG. 2 depicts a first embodiment of a method for programming the device 10 to provide the optimum hearing correction for the user. The method hinges upon the generation of a hearing loss profile for the user that indicates the nature of the user's hearing loss situation. For example, the hearing loss profile—also referred to herein as an audiogram—may be obtained from an audiologist based on audiometric testing performed on the user by the audiologist. Alternatively, the hearing loss profile may be generated by software, such as a mobile device application, that guides the user through a do-it-yourself audiometric testing process. In yet another embodiment, audiometric testing information needed to generate the hearing loss profile may be acquired by the device 10 itself, such as by implementing an audiometric testing routine as described in U.S. Pat. No. 8,472,634, the entire contents of which are incorporated herein by reference. This audiometric testing information may be uploaded from the device 10 via the wireless interface 38 to the internet, through which it is communicated to a listening device programming entity, as described below.

Figures 3, 4:
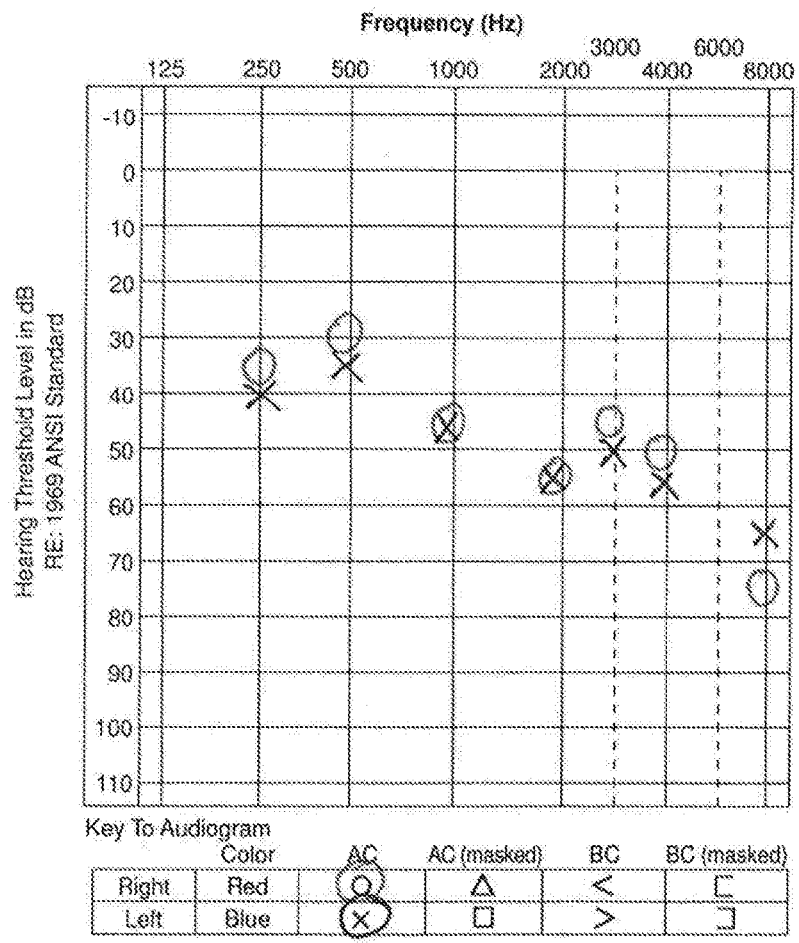
FIG. 3 depicts an example of an audiogram in graphical format as a plot of hearing threshold level versus frequency.
FIG. 4 depicts an example of the audiogram of FIG. 3 in tabular format.

The hearing loss profile may be represented as an audiogram in graphical format as depicted in FIG. 3 or in tabular form as depicted in FIG. 4. In either format, the audiogram indicates the compensation amplification (such as in decibels) needed as a function of frequency (such as in hertz) across the audible band to properly enhance the user's hearing.

In the first embodiment depicted in FIG. 2, the user or audiologist sends the user's hearing loss profile to a hearing assistance device programming entity, which may be the manufacturer of the device 10 or another entity tasked with initially programming the device for the user. The hearing assistance device programming entity receives the hearing loss profile (step 102) and based thereon determines a best-fit hearing correction algorithm for the user (step 104). In general terms, this best-fit algorithm defines the optimum amplitude-versus-frequency compensation function to be programmed into the device 10 to compensate for the user's hearing loss as indicated by the hearing loss profile. It will be appreciated that the shape of the hearing loss profile could vary substantially from one person to another, which is why it is preferable to begin the device programming process with a correction algorithm that is customized for the particular user.

The hearing assistance device programming entity uploads the best-fit hearing correction algorithm to the memory location within the memory 26 of the device 10 that is designated for the default compensation algorithm (step 106). In this manner, when the device 10 is initially powered on (or reset after the initial power-on), the best-fit hearing correction algorithm will be the default algorithm loaded from the memory 26 first. The hearing assistance device programming entity then ships the preprogrammed device 10 to the user (step 108).

In a preferred embodiment, when the user powers up the device 10 for the first time, such as by inserting the battery 30, the processor 16 loads and runs a setup program to direct the user through an initial setup procedure (step 110). In one embodiment, guidance through the setup procedure may be provided by audible instructions given to the user via the audio output section 24 of the device 10, wherein the user is audibly directed to use the up/down buttons of the rocker switch 32 to control the device 10 during setup. In an alternative embodiment, guidance through the setup procedure is provided by audiovisual instructions given to the user via a mobile device application running on the mobile computing device 40 that is communicating with the device 10 via the wireless interface 38. In this embodiment, the user may control the device 10 during setup by pressing virtual buttons displayed on the mobile computing device 40 based on instructions generated by the mobile device application.

In the embodiment in which the user is guided through the setup procedure using the mobile device application, the user may first be prompted to install the battery into the device 10 (step 110). The user may then be prompted to indicate which of the user's ears has better hearing, such as by pressing a virtual button to select left ear, or right ear, or no difference. The mobile device application may then display a first series of buttons on the mobile device screen, such as five buttons labeled 1 through 5, each corresponding to a particular hearing compensation algorithm stored in the device memory 26. In a preferred embodiment, one of the buttons corresponds to the best-fit hearing correction algorithm that was uploaded to the device at step 106. The other buttons preferably correspond to a first set of preloaded hearing correction algorithms that are generally used to compensate for normal patterns of hearing loss experienced by a wide range of hearing-impaired persons. The user may be prompted to have a conversation with someone while sequentially trying out each of the hearing correction algorithms that are selectable using the virtual buttons (step 112). After trying each one, the user selects the best sounding algorithm (step 114) and either confirms the selection or goes back to step 112 to start over (step 116).

In a preferred embodiment, the mobile device application may then display a second series of buttons on the mobile device screen, each corresponding to a particular hearing compensation algorithm stored in the device memory 26. In a preferred embodiment, one of the buttons corresponds to the currently-selected hearing correction algorithm (selected at step 114), and the other buttons preferably correspond to a second set of preloaded hearing correction algorithms that are slight variations from the first set of preloaded hearing correction algorithms. The user may be prompted to again have a conversation with someone while sequentially trying out each of the hearing correction algorithms that are selectable using the virtual buttons (step 118). After trying each one, the user selects the best sounding algorithm (step 120), which becomes the default algorithm that will stay in use until the user decides to reset and reprogram the device 10 (step 122). In a preferred embodiment, when the user resets the device 10, the original best-fit hearing correction algorithm that was uploaded at step 106 again becomes the default algorithm, and the setup procedure can be repeated beginning at step 112.

Figure 5:
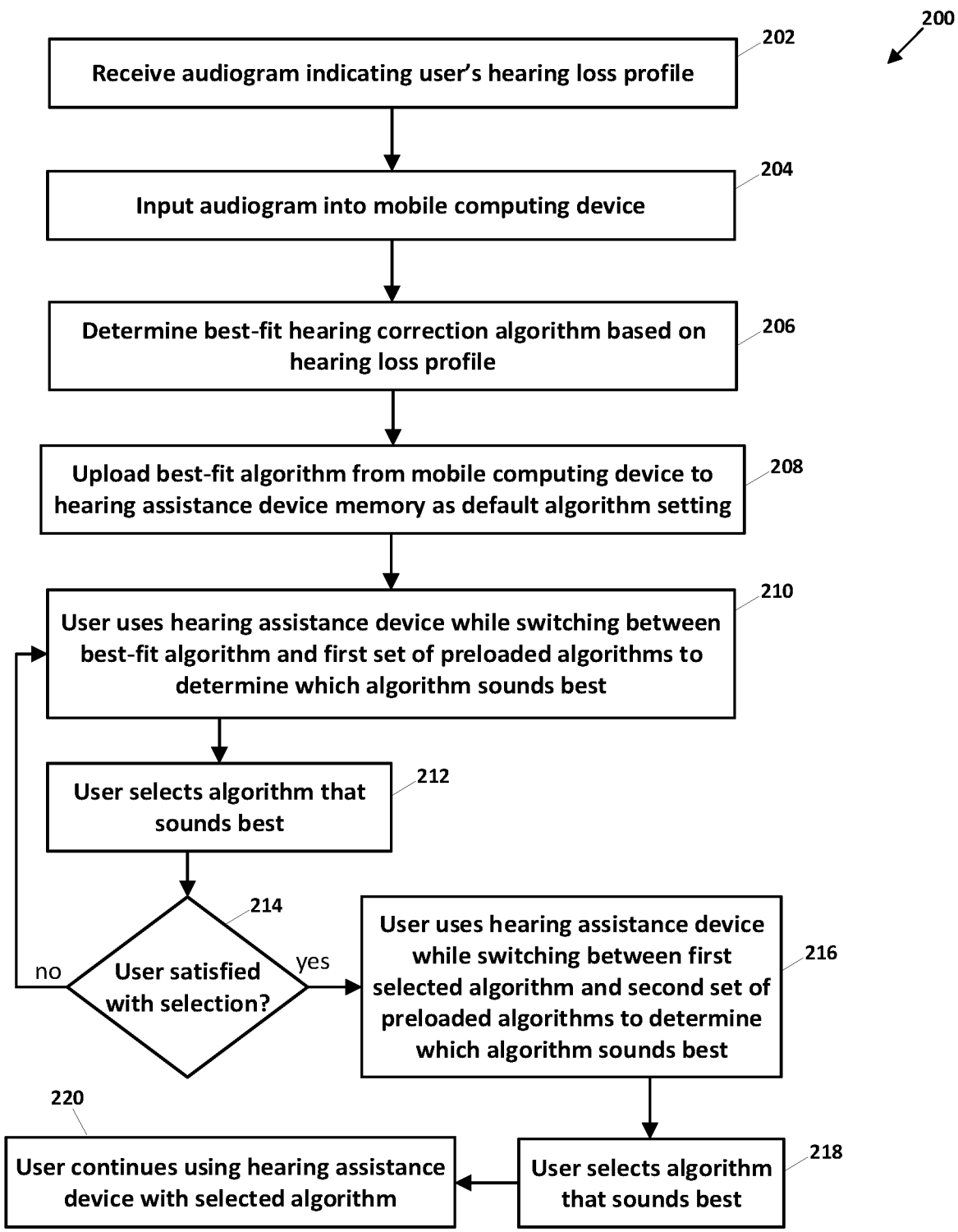
FIG. 5 depicts a functional flow diagram of the operation of a personal hearing assistance device according to an alternative embodiment.

In a second embodiment depicted in FIG. 5, the user receives an audiogram indicating the user's hearing loss profile from an audiologist or other entity that generated the audiogram based on a hearing test of the user (step 202). The user or someone else then inputs the audiogram into a mobile computing device 40, such as the user's smartphone, using an application running on the device 40 (step 204). In a preferred embodiment, the application generates a graphical user interface (GUI) display on the device 40 that prompts the user to input the hearing threshold level values for each tested frequency from the user's audiogram. For example, if the device 10 being programmed is for use in the left ear, the application may first generate a prompt that says "Enter the left ear hearing threshold level (in dB) at 250 Hz," in response to which the user enters the number "40" using the application GUI. This input procedure is then repeated for each of the other available frequencies in the audiogram for the left ear (500 Hz, 750 Hz, 1000 Hz, etc.) until the complete left ear audiogram has been input.

Using the entered audiogram values, the application running on the device 40 generates a best-fit hearing correction algorithm for the user (step 206). In general terms, this best-fit algorithm defines the optimum amplitude-versus-frequency compensation function to be programmed into the device 10 to compensate for the user's hearing loss as indicated by the entered audiogram values. The application running on the device 40 next causes the device 40 to wirelessly transmit the best-fit hearing correction algorithm to the hearing assistance device 10, such as via a Bluetooth connection, and the algorithm is uploaded to the memory location within the memory 26 of the device 10 that is designated for the default compensation algorithm (step 208). In this manner, when the device 10 is initially powered on (or reset after the initial power-on), the best-fit hearing correction algorithm will be the default algorithm loaded from the memory 26 first.

As in the previously described embodiment, the user is then guided through the rest of the setup procedure by prompts from the mobile device application. For example, the mobile device application may display a first series of buttons on the mobile device screen, such as five buttons labeled 1 through 5, each corresponding to a particular hearing compensation algorithm stored in the device memory 26. In a preferred embodiment, one of the buttons corresponds to the best-fit hearing correction algorithm that was uploaded to the device at step 106. The other buttons preferably correspond to a first set of preloaded hearing correction algorithms that are generally used to compensate for normal patterns of hearing loss experienced by a wide range of hearing-impaired persons. The user may be prompted to have a conversation with someone while sequentially trying out each of the hearing correction algorithms that are selectable using the virtual buttons (step 210). After trying each one, the user selects the best sounding algorithm (step 212) and either confirms the selection or goes back to step 210 to start over (step 214).

As in the previously described embodiment, the mobile device application may then display a second series of buttons on the mobile device screen, each corresponding to a particular hearing compensation algorithm stored in the device memory 26. In a preferred embodiment, one of the buttons corresponds to the currently-selected hearing correction algorithm (selected at step 212), and the other buttons preferably correspond to a second set of preloaded hearing correction algorithms that are slight variations from the first set of preloaded hearing correction algorithms. The user may be prompted to again have a conversation with someone while sequentially trying out each of the hearing correction algorithms that are selectable using the virtual buttons (step 216). After trying each one, the user selects the best sounding algorithm (step 218), which becomes the default algorithm that will stay in use until the user decides to reset and reprogram the device 10 (step 220). If the user resets the device 10, the original best-fit hearing correction algorithm that was uploaded at step 208 again becomes the default algorithm, and the setup procedure can be repeated beginning at step 210.

Other aspects of various embodiments of the device 10 and its programming and operational methods are described in the following U.S. patents, the entire contents of which are incorporated herein by reference: U.S. Pat. Nos. 7,974,716, 8,265,314, 8,284,968, 8,396,237, 8,077,890, and 8,472,634.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for programming a programmable hearing assistance device having memory in which one or more preloaded hearing correction algorithms are stored, the method comprising:
    (a) receiving a hearing loss profile of a user of the programmable hearing assistance device;
    (b) based at least in part on the hearing loss profile, determining a preferred hearing correction algorithm for the user;
    (c) storing the preferred hearing correction algorithm into the memory of the programmable hearing assistance device, after which the memory contains the preferred hearing correction algorithm and the one or more preloaded hearing correction algorithms;
    (d) after completion of step (c), delivering the programmable hearing assistance device to the user;
    (e) during an initial setup procedure performed by the user, the user manually switching between the preferred hearing correction algorithm and the one or more preloaded hearing correction algorithms, and listening to sounds amplified by the programmable hearing assistance device while using the preferred hearing correction algorithm or while using one of the preloaded hearing correction algorithms; and
    (f) the user selecting the preferred hearing correction algorithm or one of the one or more preloaded hearing correction algorithms for continued use in the programmable hearing assistance device,
wherein the algorithm selected in step (f) comprises a selected algorithm that continues to be used in the programmable hearing assistance device after completion of the initial setup procedure.

2. The method of claim 1 wherein steps (e) and (f) further comprise:
    (e1) the user listening to sounds amplified by the programmable hearing assistance device while switching between the preferred hearing correction algorithm and one or more first preloaded hearing correction algorithms;
    (f1) the user selecting the preferred hearing correction algorithm or one of the one or more first preloaded hearing correction algorithms;
    (e2) the user listening to sounds amplified by the programmable hearing assistance device while switching between the algorithm selected in step (f1) and one or more second preloaded hearing correction algorithms; and
    (f2) the user selecting the algorithm selected in step (f1) or one of the one or more second preloaded hearing correction algorithms for continued use in the programmable hearing assistance device.

3. The method of claim 1 wherein the hearing loss profile received in step (a) is generated by an audiologist.

4. The method of claim 1 wherein the hearing loss profile comprises an audiogram.

5. The method of claim 1 wherein steps (a) through (c) are performed by a hearing assistance device programming entity.

6. The method of claim 5 wherein the hearing assistance device programming entity is a manufacturer of the programmable hearing assistance device.

7. The method of claim 5 wherein the hearing assistance device programming entity is an audiologist.

8. The method of claim 1 wherein the selected algorithm continues to be used each time power is applied to the programmable hearing assistance device until the programmable hearing assistance device is reset or reprogrammed.

9. The method of claim 1 wherein the switching and selecting of steps (e) and (f) are performed by the user while interacting with an interface of a mobile computing device.

10. The method of claim 9 wherein the mobile computing device comprises a smart phone or tablet computer executing a setup and control application.

11. A method for programming a programmable hearing assistance device having memory in which one or more preloaded hearing correction algorithms are stored, the method comprising:
    (a) entering an audiogram into memory of a mobile computing device, the audiogram indicating a hearing loss profile of a user of the programmable hearing assistance device;
    (b) based at least in part on the audiogram, a processor of the mobile computing device determining a preferred hearing correction algorithm for the user;
    (c) communicating the preferred hearing correction algorithm from the mobile computing device to the memory of the programmable hearing assistance device;
    (d) storing the preferred hearing correction algorithm into the memory of the programmable hearing assistance device, after which the memory of the programmable hearing assistance device contains the preferred hearing correction algorithm and the one or more preloaded hearing correction algorithms;
    (e) during an initial setup procedure performed by the user, the user manually switching between the preferred hearing correction algorithm and the one or more preloaded hearing correction algorithms, and listening to sounds amplified by the programmable hearing assistance device while using the preferred hearing correction algorithm or while using one of the preloaded hearing correction algorithms; and
    (f) the user selecting the preferred hearing correction algorithm or one of the one or more preloaded hearing correction algorithms for continued use in the programmable hearing assistance device.

12. The method of claim 11 wherein the algorithm selected in step (f) continues in use each time power is applied to the programmable hearing assistance device until the programmable hearing assistance device is reset or reprogrammed.

13. The method of claim 11 wherein the switching and selecting of steps (e) and (f) are performed by the user while interacting with an interface of the mobile computing device.

14. The method of claim 13 wherein the interface of the mobile computing device comprises a graphical user interface displayed on a display screen of the mobile computing device.

15. The method of claim 11 wherein the mobile computing device is in wireless communication with the programmable hearing assistance device, and step (c) is performed wirelessly.

16. The method of claim 11 wherein the mobile computing device comprises a smart phone or tablet computer executing a setup and control application.

17. The method of claim 11 wherein the one or more preloaded hearing correction algorithms were loaded into the memory of the programmable hearing assistance device prior to step (d).

18. A memory storage device on which computer-executable instructions are stored for downloading to and execution by a processor of a mobile computing device to program a programmable hearing assistance device having memory in which multiple preloaded hearing correction algorithms are stored, the computer-executable instructions comprising instructions for:
  entering an audiogram into memory of the mobile computing device, the audiogram indicating a hearing loss profile of a user of the programmable hearing assistance device;
  based at least in part on the audiogram, determining a preferred hearing correction algorithm for the user;
  communicating the preferred hearing correction algorithm from the mobile computing device to the programmable hearing assistance device;
  controlling the programmable hearing assistance device to store the preferred hearing correction algorithm into the memory of the programmable hearing assistance device, after which the memory of the programmable hearing assistance device contains the preferred hearing correction algorithm and the multiple preloaded hearing correction algorithms;
  based on input from the user, manually controlling the programmable hearing assistance device to switch between the preferred hearing correction algorithm and the multiple preloaded hearing correction algorithms while the user listens to sounds amplified by the programmable hearing assistance device; and
  based on input from the user, selecting the preferred hearing correction algorithm or one of the preloaded hearing correction algorithms for continued use in the programmable hearing assistance device.

19. The memory storage device of claim 18 wherein the computer-executable instructions comprise instructions for generating a graphical user interface displayed on a display screen of the mobile computing device, the graphical user interface for receiving the input from the user.

20. The memory storage device of claim 18 wherein the computer-executable instructions comprise instructions for wirelessly communicating the preferred hearing correction algorithm from the mobile computing device to the programmable hearing assistance device.

* * * * *